(12) United States Patent
McGuckin, Jr. et al.

(10) Patent No.: US 7,331,976 B2
(45) Date of Patent: Feb. 19, 2008

(54) DISTAL PROTECTION DEVICE

(75) Inventors: James F. McGuckin, Jr., Radnor, PA (US); Marc Alan Levine, Pottstown, PA (US); James Erich Bressler, Langhorne, PA (US)

(73) Assignee: Rex Medical, L.P., Conshohocken, PA (US)

( * ) Notice: Subject to any disclaimer, the term of this patent is extended or adjusted under 35 U.S.C. 154(b) by 371 days.

(21) Appl. No.: 10/800,298

(22) Filed: Mar. 12, 2004

(65) Prior Publication Data

US 2004/0236368 A1 Nov. 25, 2004

Related U.S. Application Data

(60) Provisional application No. 60/466,491, filed on Apr. 29, 2003.

(51) Int. Cl.
*A61F 2/01* (2006.01)

(52) U.S. Cl. .................. 606/200; 606/113; 623/1.1

(58) Field of Classification Search ............ None
See application file for complete search history.

(56) References Cited

U.S. PATENT DOCUMENTS

| | | | |
|---|---|---|---|
| 4,425,908 A * | 1/1984 | Simon | ............... 128/899 |
| 4,873,978 A | 10/1989 | Ginsburg | |
| 5,100,423 A | 3/1992 | Fearnot | |
| 5,192,286 A | 3/1993 | Phan et al. | |
| 5,421,832 A | 6/1995 | Lefebvre | |
| 5,626,602 A | 5/1997 | Gianotti et al. | |
| 5,658,296 A | 8/1997 | Bates et al. | |
| 5,720,764 A | 2/1998 | Naderlinger | |
| 5,814,064 A | 9/1998 | Daniel et al. | |
| 5,827,324 A | 10/1998 | Cassell et al. | |
| 5,848,964 A | 12/1998 | Samuels | |
| 5,941,896 A | 8/1999 | Kerr | |
| 5,972,019 A * | 10/1999 | Engelson et al. | ............ 606/200 |
| 5,984,947 A | 11/1999 | Smith | |
| 6,001,118 A | 12/1999 | Daniel et al. | |
| 6,027,520 A | 2/2000 | Tsugita et al. | |
| 6,056,770 A * | 5/2000 | Epstein et al. | .............. 606/213 |
| 6,066,149 A * | 5/2000 | Samson et al. | ............. 606/159 |
| 6,066,158 A * | 5/2000 | Engelson et al. | .......... 606/200 |
| 6,080,178 A | 6/2000 | Meglin | |
| 6,096,053 A | 8/2000 | Bates | |
| 6,123,715 A | 9/2000 | Amplatz | |
| 6,129,739 A | 10/2000 | Khosravi | |
| 6,146,396 A | 11/2000 | Kónya et al. | |
| 6,152,946 A | 11/2000 | Broome et al. | |

(Continued)

FOREIGN PATENT DOCUMENTS

WO    WO 9601591    1/1996

(Continued)

*Primary Examiner*—Glenn K. Dawson
(74) *Attorney, Agent, or Firm*—Neil D. Gershon

(57) ABSTRACT

A distal protection device comprising a catheter having a first strut movable from a collapsed configuration to an expanded configuration having a first dimension and a second strut movable from a collapsed configuration to an expanded configuration having a second dimension larger than the first dimension. Movement of the first strut deploys filter material to a first position having a first deployed dimension and movement of the second strut to a first position deploys filter material to a second deployed dimension larger than the first expanded dimension.

3 Claims, 13 Drawing Sheets

U.S. PATENT DOCUMENTS

| | | |
|---|---|---|
| 6,168,579 B1 | 1/2001 | Tsugita |
| 6,171,327 B1 | 1/2001 | Daniel et al. |
| 6,179,851 B1 | 1/2001 | Barbut et al. |
| 6,179,861 B1 * | 1/2001 | Khosravi et al. ........... 606/200 |
| 6,187,025 B1 | 2/2001 | Machek |
| 6,224,620 B1 | 5/2001 | Maahs |
| 6,245,088 B1 | 6/2001 | Lowery |
| 6,258,115 B1 | 7/2001 | Dubrul |
| 6,264,672 B1 | 7/2001 | Fisher |
| 6,277,139 B1 | 8/2001 | Levinson et al. |
| 6,290,710 B1 | 9/2001 | Cryer et al. |
| 6,336,934 B1 | 1/2002 | Gilson et al. |
| 6,338,735 B1 | 1/2002 | Stevens |
| 6,340,364 B2 | 1/2002 | Kanesaka |
| 6,346,116 B1 | 2/2002 | Brooks et al. |
| 6,348,056 B1 * | 2/2002 | Bates et al. ................. 606/114 |
| 6,364,895 B1 | 4/2002 | Greenhalgh |
| 6,364,900 B1 | 4/2002 | Heuser |
| 6,368,338 B1 | 4/2002 | Kónva et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,425,909 B1 | 7/2002 | Dieck et al. |
| 6,482,222 B1 | 11/2002 | Bruckheimer et al. |
| 6,485,501 B1 | 11/2002 | Green |
| 6,500,191 B2 | 12/2002 | Addis |
| 6,530,939 B1 | 3/2003 | Hopkins et al. |
| 6,544,279 B1 | 4/2003 | Hopkins et al. |
| 6,551,268 B1 | 4/2003 | Kaganov et al. |
| 6,558,405 B1 | 5/2003 | McInnes |
| 6,562,058 B2 * | 5/2003 | Seguin et al. ................ 606/200 |
| 6,569,184 B2 | 5/2003 | Huter |
| 6,582,448 B1 | 6/2003 | Boyle et al. |
| 6,589,263 B1 | 7/2003 | Hopkins et al. |
| 6,592,606 B2 | 7/2003 | Huter et al. |
| 6,592,616 B1 | 7/2003 | Stack et al. |
| 6,596,011 B2 | 7/2003 | Johnson et al. |
| 6,605,102 B1 * | 8/2003 | Mazzocchi et al. ......... 606/200 |
| 6,610,077 B1 | 8/2003 | Hancock et al. |
| 6,616,679 B1 | 9/2003 | Khosravi et al. |
| 6,616,680 B1 | 9/2003 | Thielen |
| 6,620,182 B1 | 9/2003 | Khosravi et al. |
| 6,635,068 B1 | 10/2003 | Dubrul et al. |
| 6,635,070 B2 | 10/2003 | Leeflang et al. |
| 6,638,294 B1 | 10/2003 | Palmer |
| 6,645,220 B1 | 11/2003 | Huter et al. |
| 6,645,223 B2 | 11/2003 | Boyle et al. |
| 6,652,505 B1 | 11/2003 | Tsugita |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,207 B2 | 12/2003 | Epstein et al. |
| 6,660,021 B1 | 12/2003 | Palmer et al. |
| 6,663,652 B2 * | 12/2003 | Daniel et al. ................ 606/200 |
| 6,695,813 B1 | 2/2004 | Boyle et al. |
| 6,695,865 B2 | 2/2004 | Boyle et al. |
| 6,706,053 B1 | 3/2004 | Boylan et al. |
| 6,706,055 B2 | 3/2004 | Douk et al. |
| 6,716,231 B1 | 4/2004 | Rafiee et al. |
| 6,726,701 B2 | 4/2004 | Gilson et al. |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,755,847 B2 | 6/2004 | Eskuri |
| 6,761,727 B1 | 7/2004 | Ladd |
| 6,761,732 B2 | 7/2004 | Burkett et al. |
| 6,773,448 B2 | 8/2004 | Kusleika et al. |
| 6,818,006 B2 | 11/2004 | Douk et al. |
| 6,837,898 B2 | 1/2005 | Boyle et al. |
| 6,840,950 B2 * | 1/2005 | Stanford et al. ............. 606/200 |
| 6,911,036 B2 | 6/2005 | Douk et al. |
| 6,918,921 B2 | 7/2005 | Brady et al. |
| 6,929,652 B1 | 8/2005 | Andrews et al. |
| 6,936,059 B2 | 8/2005 | Belef |
| 2001/0011182 A1 | 8/2001 | Dubrul et al. |
| 2002/0095171 A1 | 7/2002 | Belef |
| 2002/0183783 A1 | 12/2002 | Shadduck |
| 2003/0004540 A1 | 1/2003 | Linder et al. |
| 2003/0004541 A1 | 1/2003 | Linder et al. |
| 2003/0045898 A1 | 3/2003 | Harrison et al. |
| 2003/0060844 A1 | 3/2003 | Borillo et al. |
| 2003/0065355 A1 | 4/2003 | Weber |
| 2003/0100917 A1 | 5/2003 | Boyle et al. |
| 2003/0100918 A1 | 5/2003 | Duane |
| 2003/0114880 A1 | 6/2003 | Hansen et al. |
| 2004/0049223 A1 * | 3/2004 | Nishtala et al. ............. 606/198 |
| 2005/0101988 A1 * | 5/2005 | Stanford et al. ............. 606/200 |
| 2005/0177187 A1 * | 8/2005 | Gray et al. .................. 606/200 |
| 2005/0216052 A1 * | 9/2005 | Mazzocchi et al. ......... 606/200 |

FOREIGN PATENT DOCUMENTS

| | | |
|---|---|---|
| WO | WO 0007521 | 2/2000 |
| WO | WO 0007655 | 2/2000 |
| WO | WO 0145590 | 6/2001 |

* cited by examiner

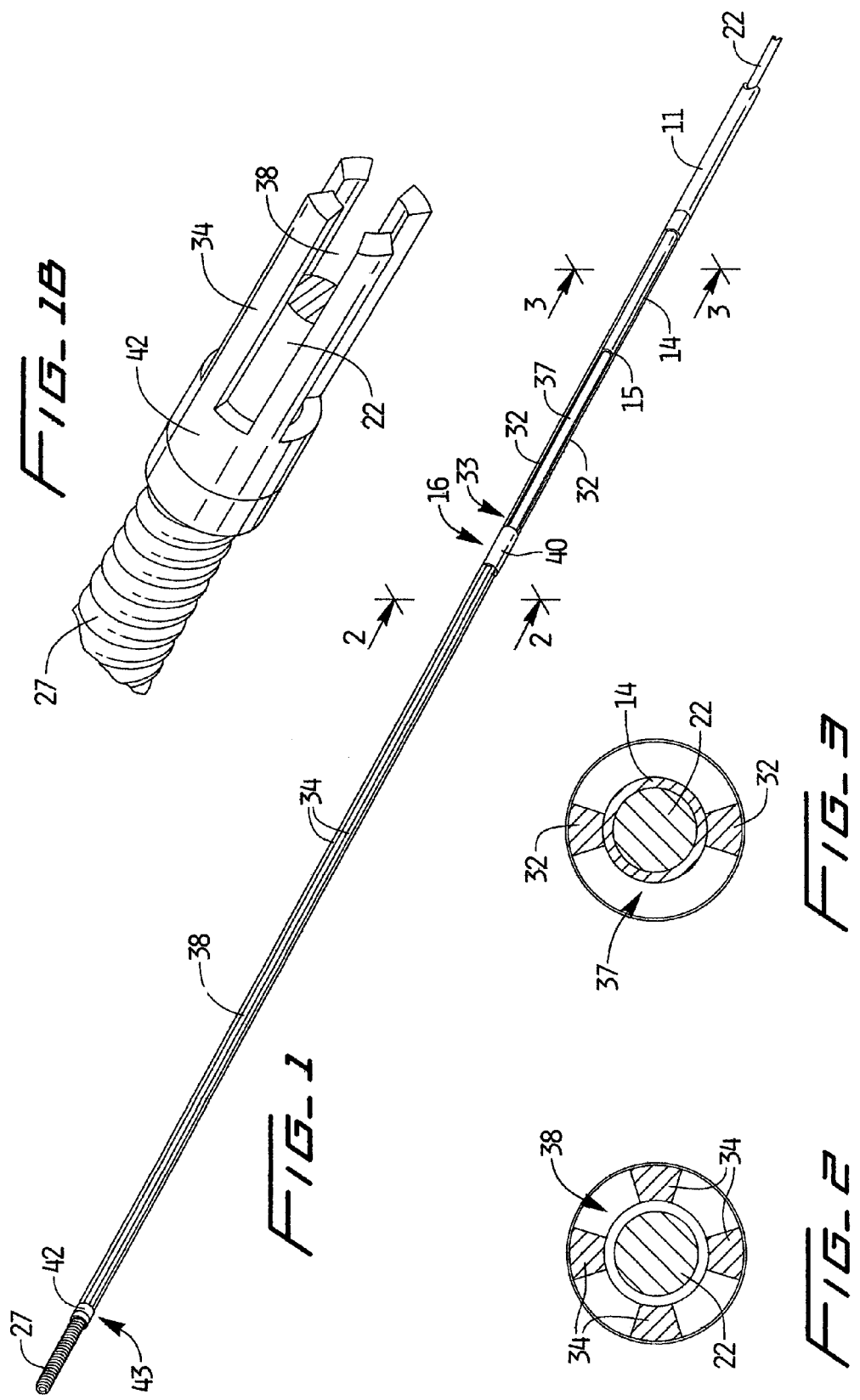

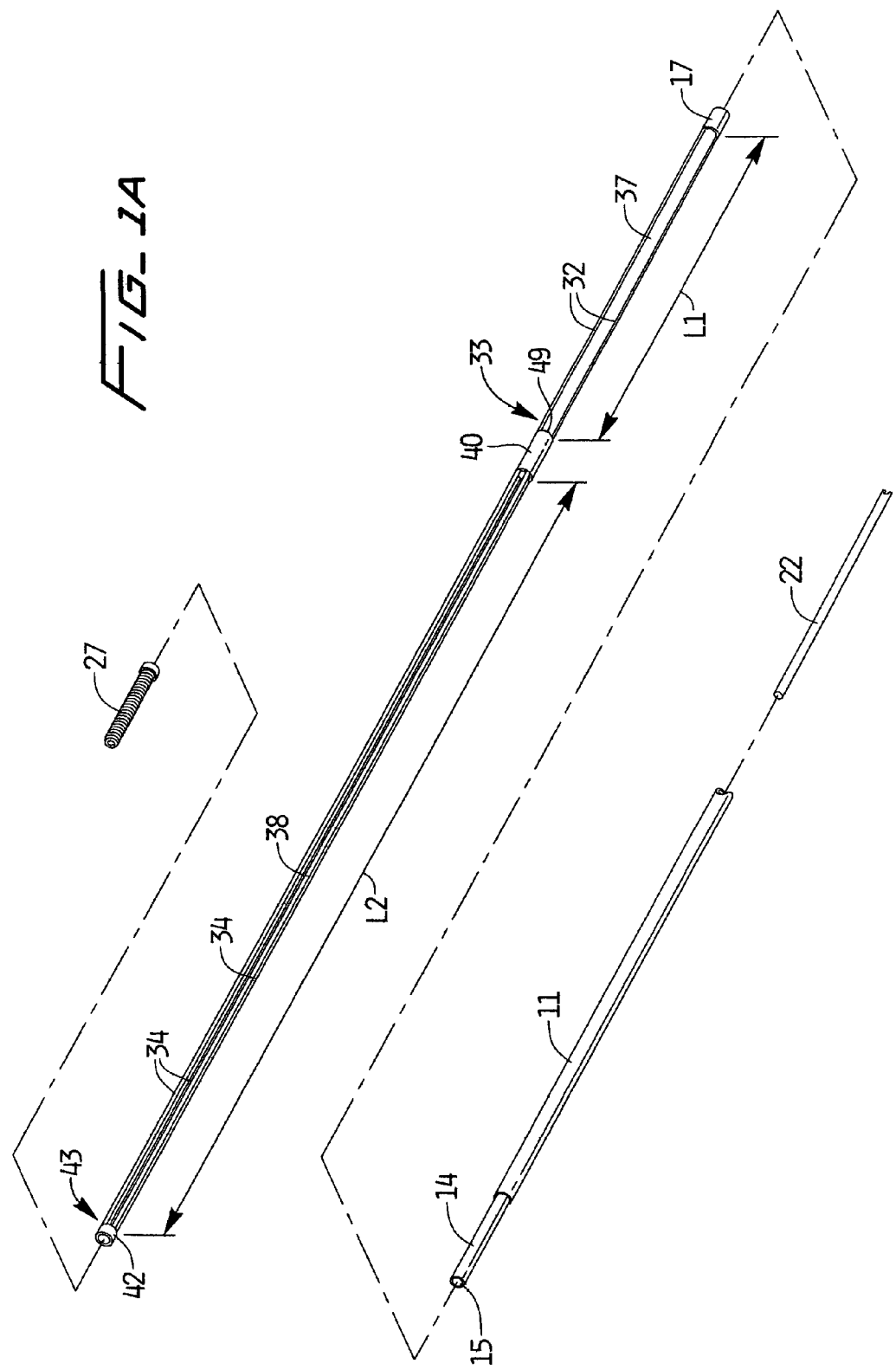

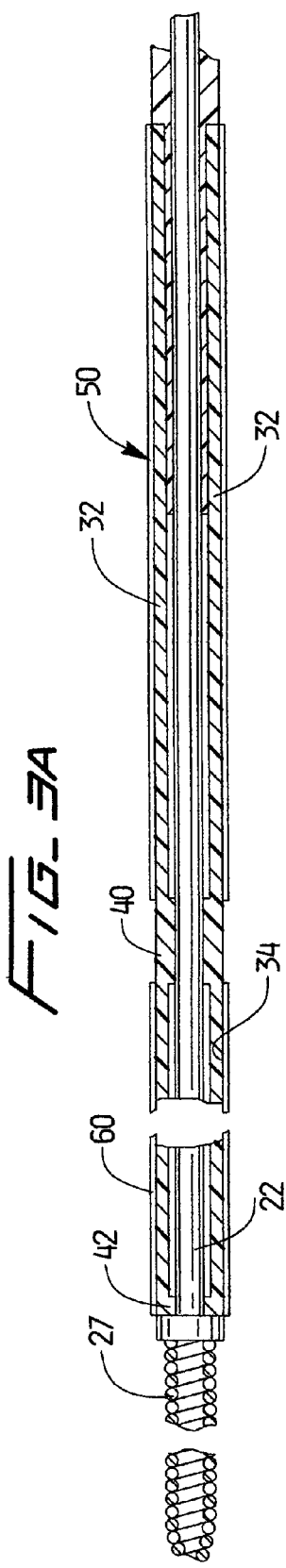
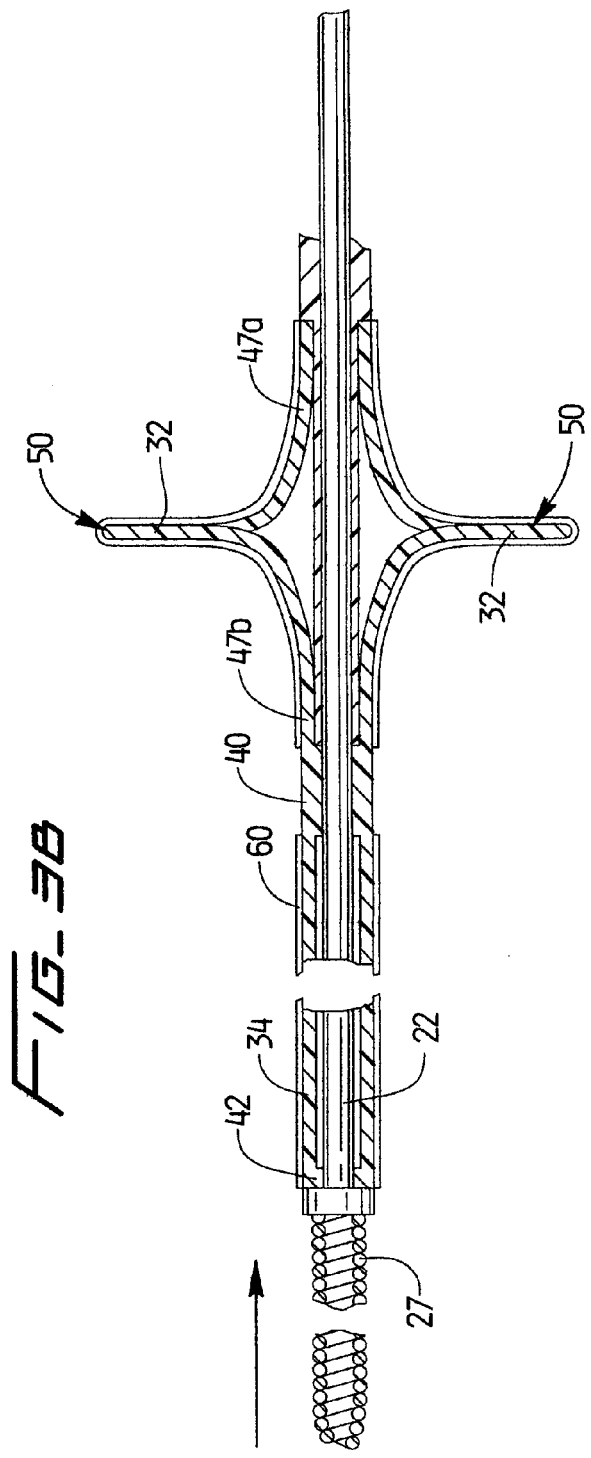

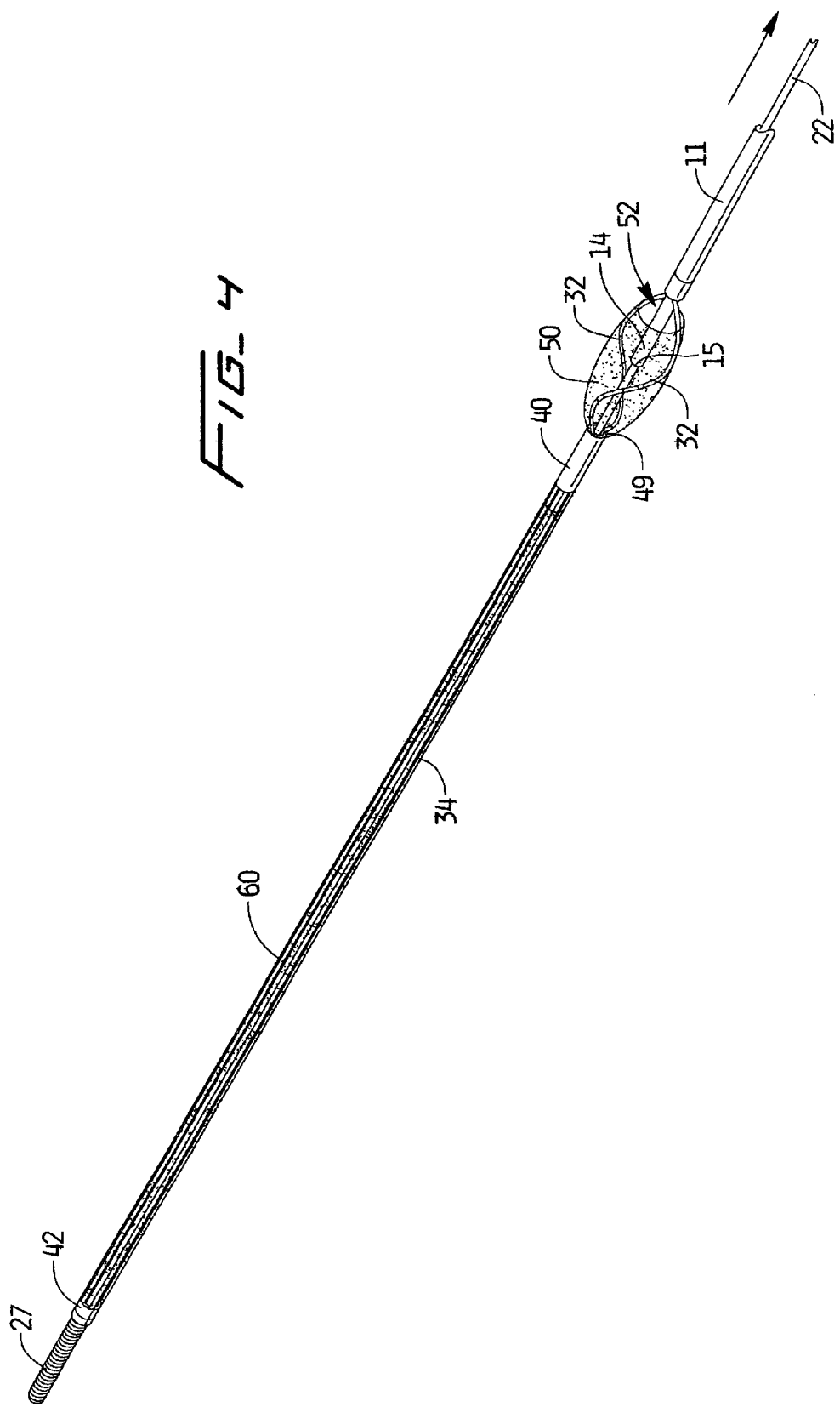

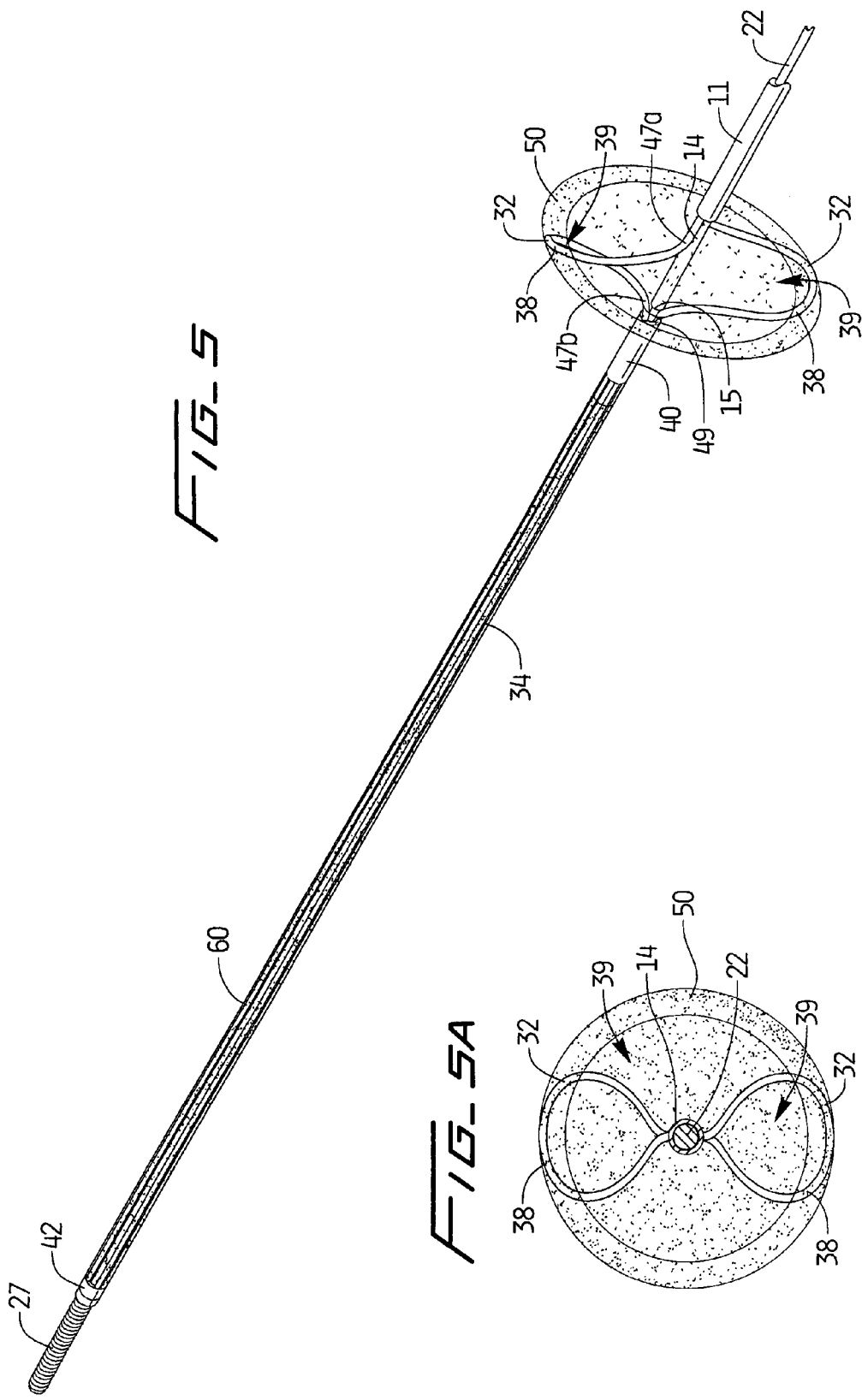

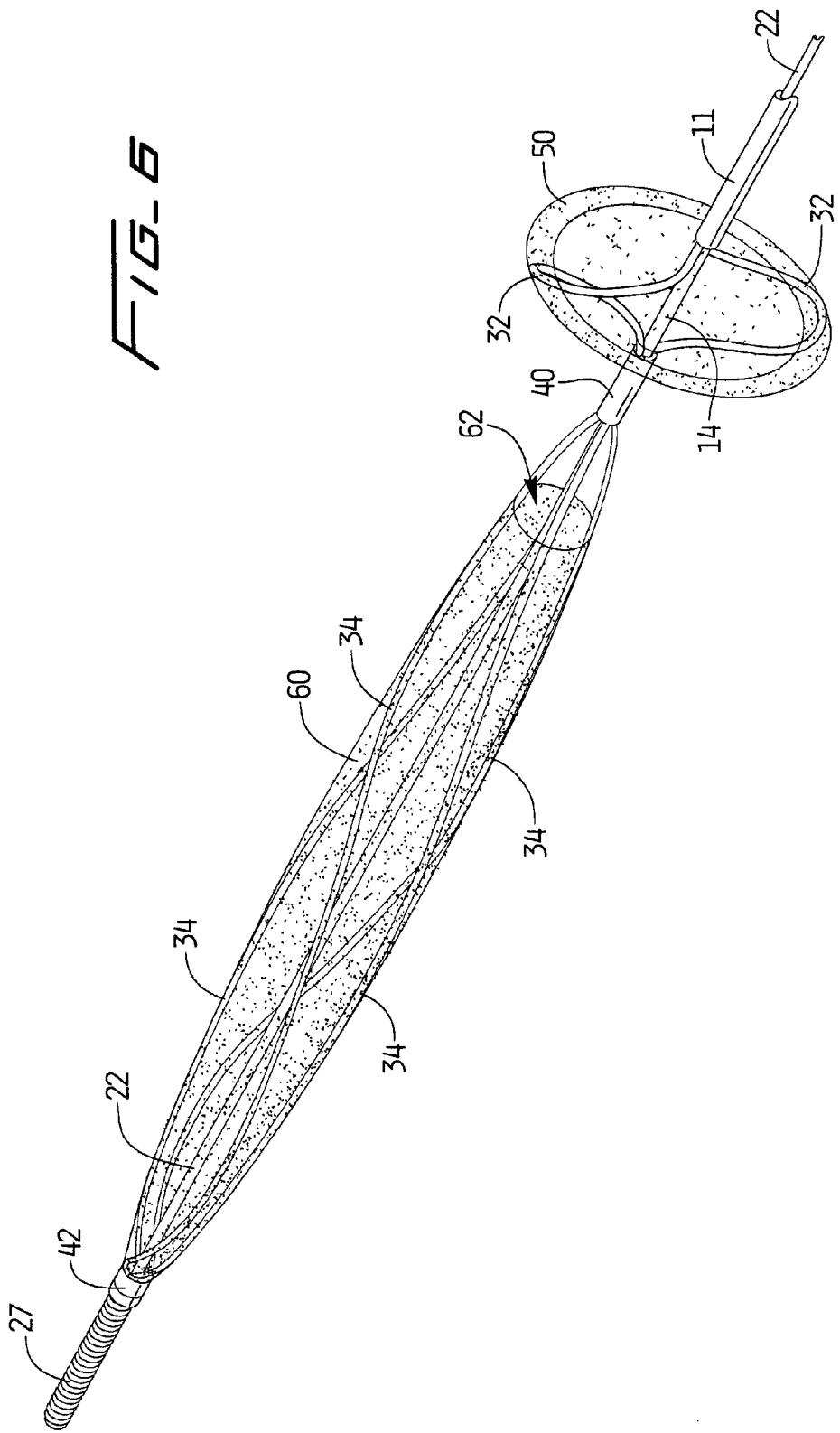

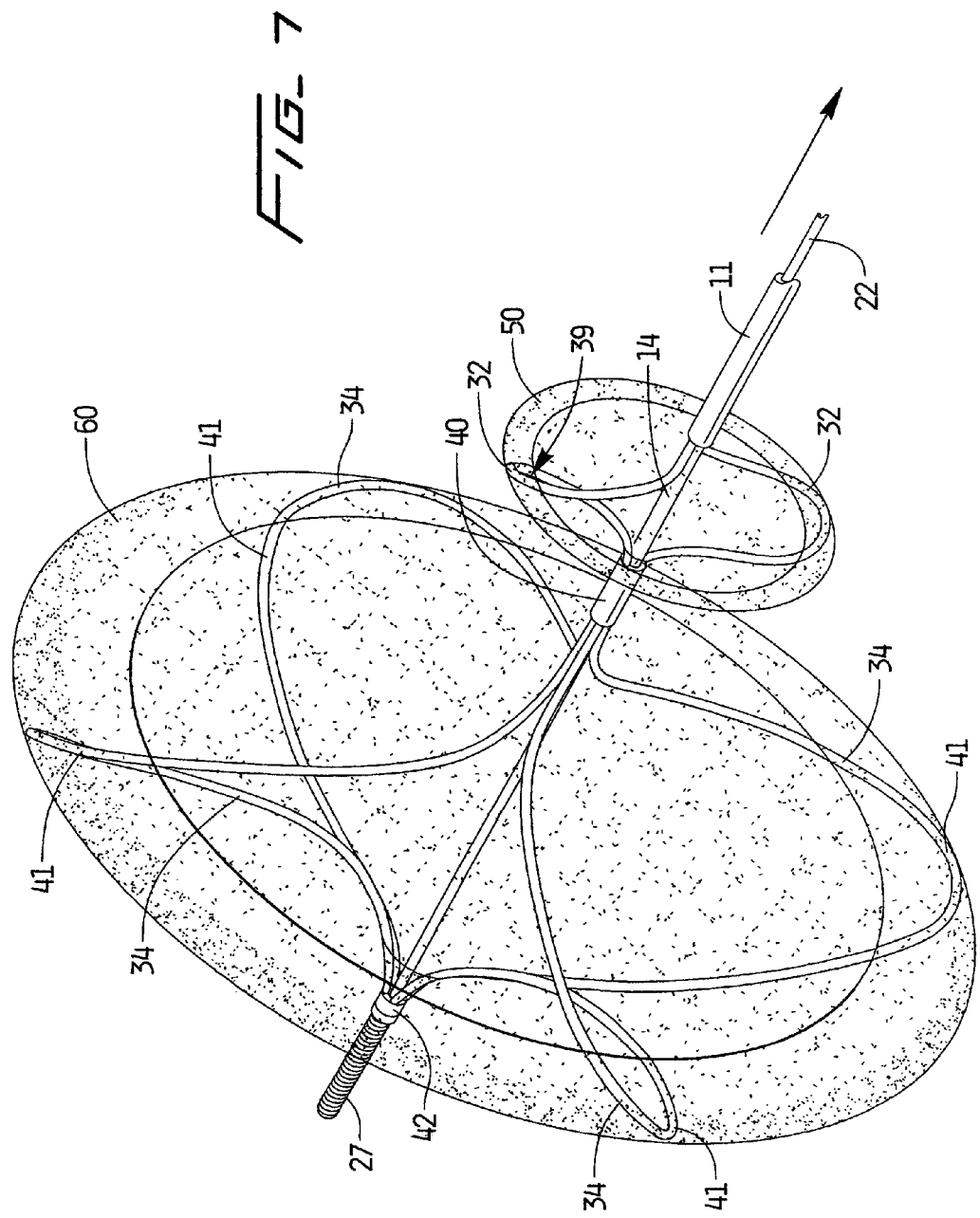

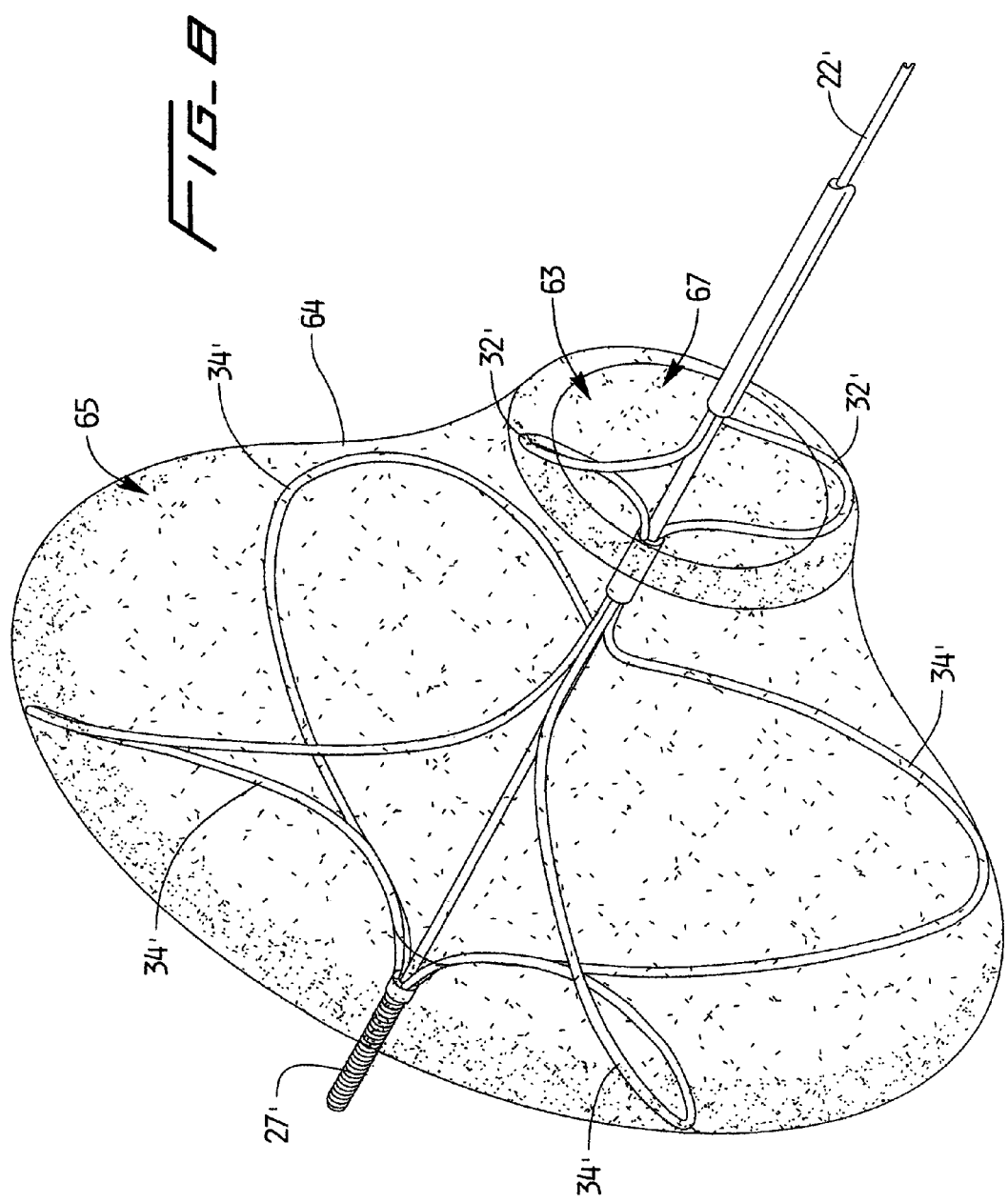

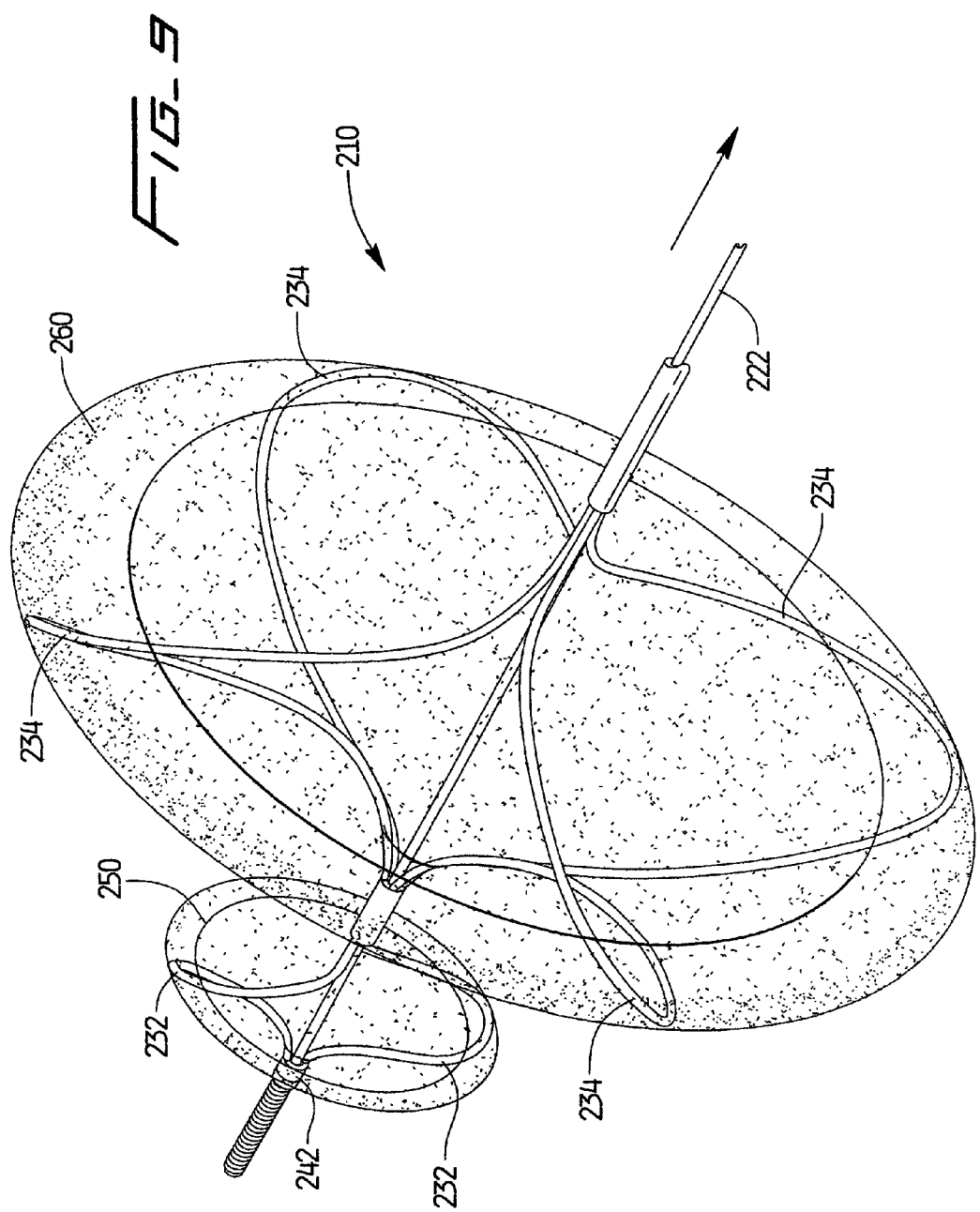

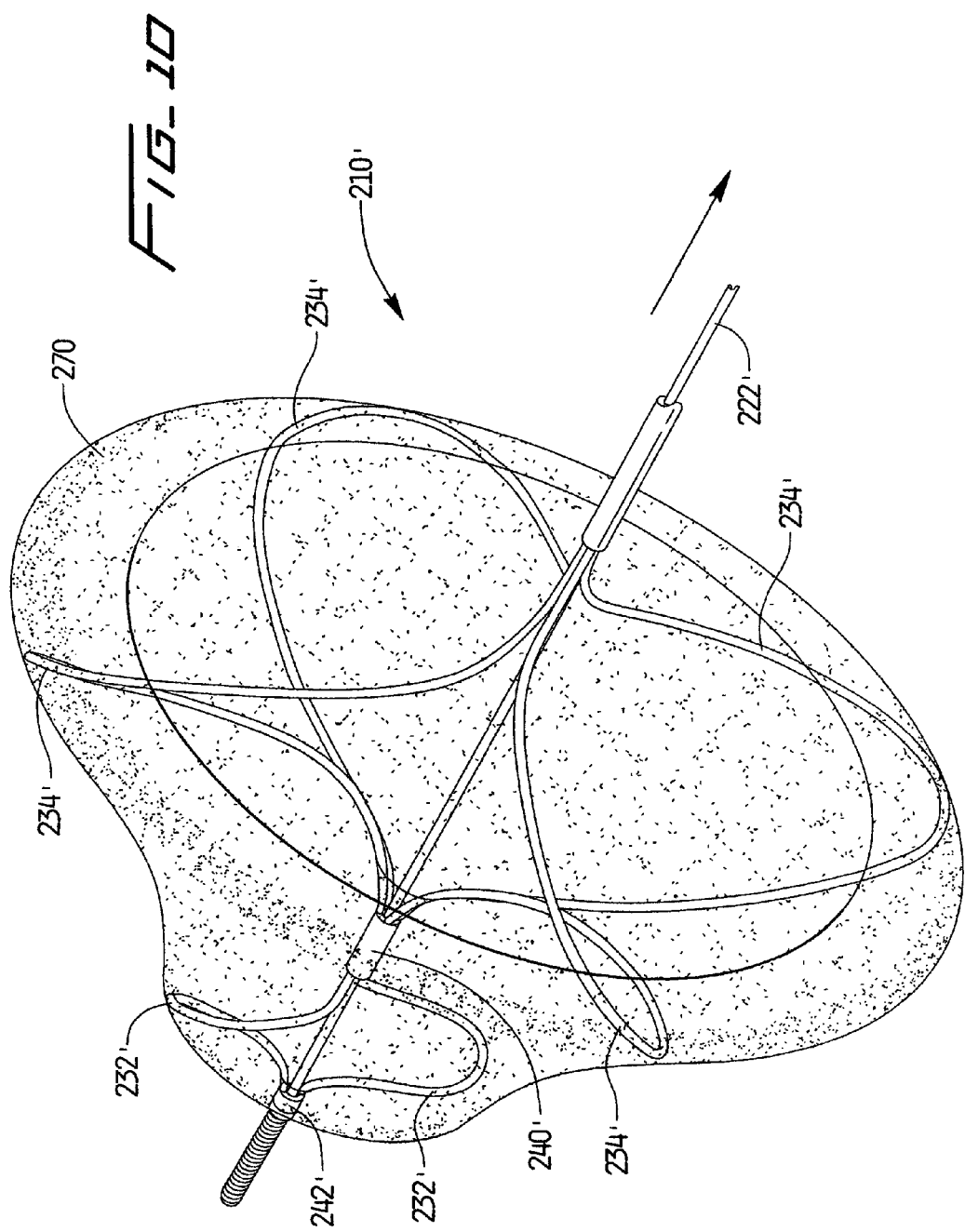

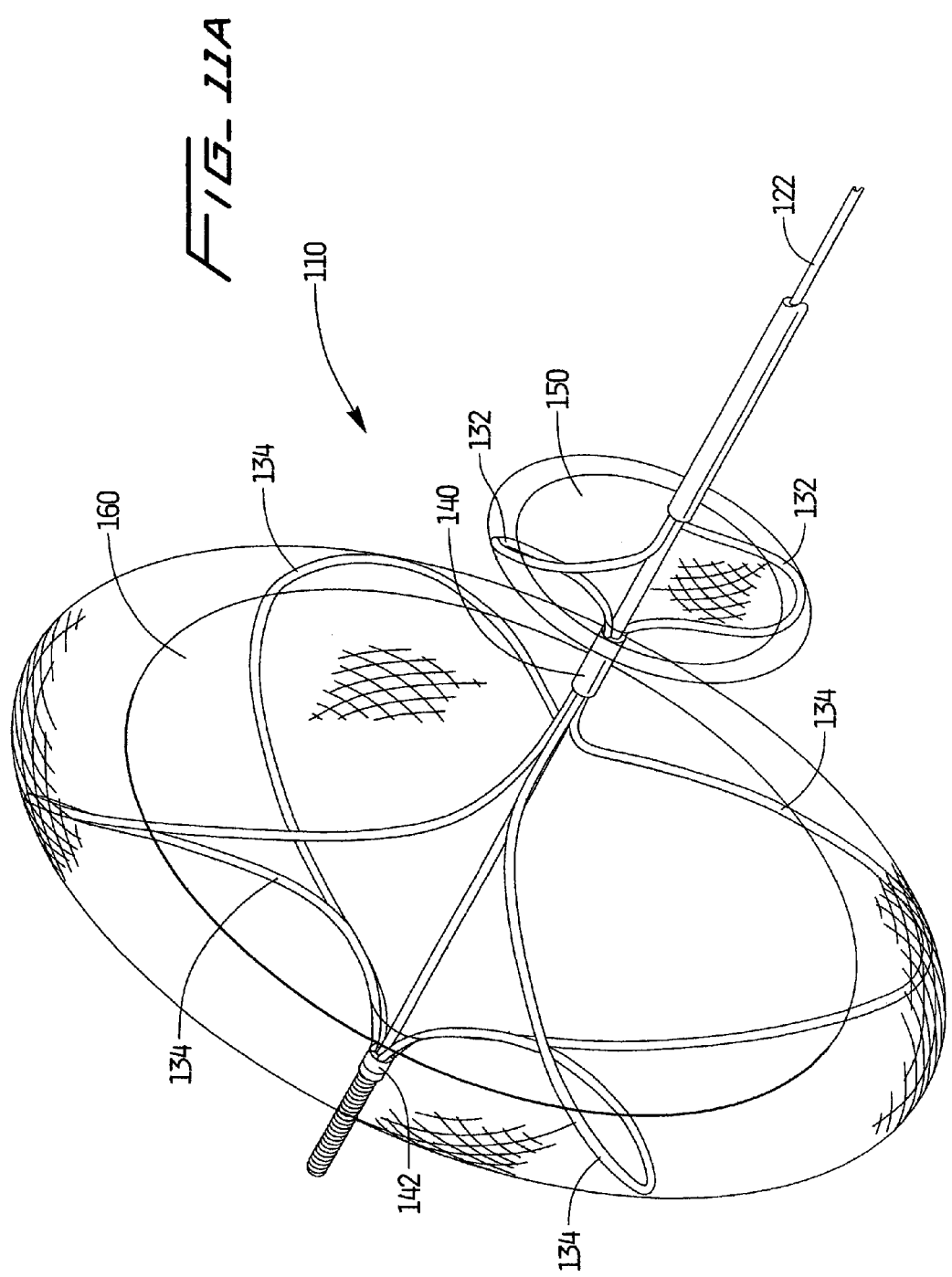

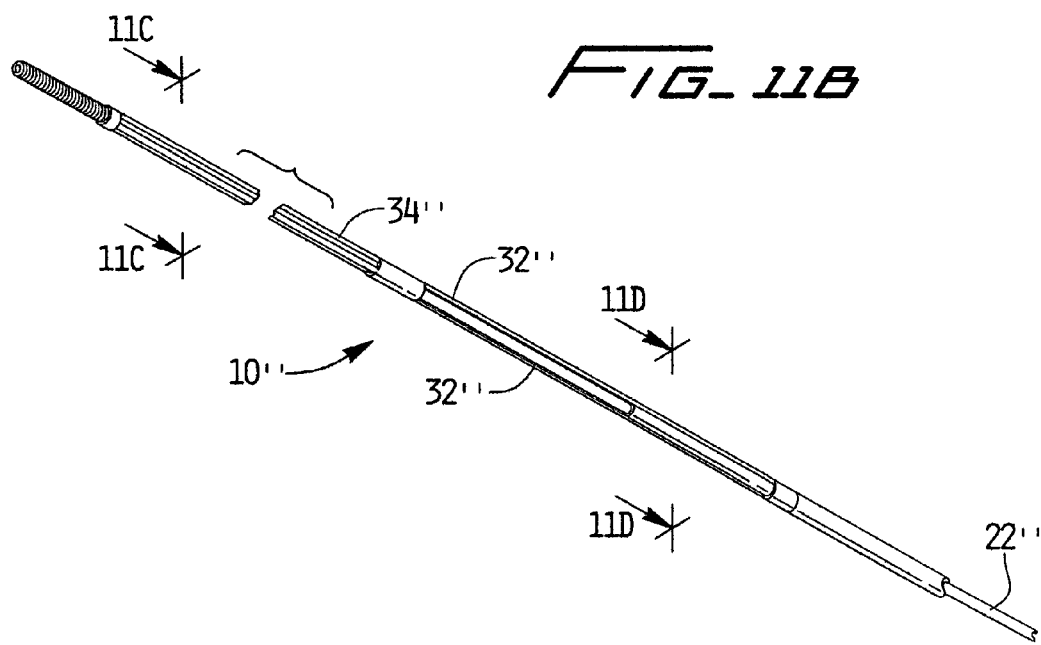
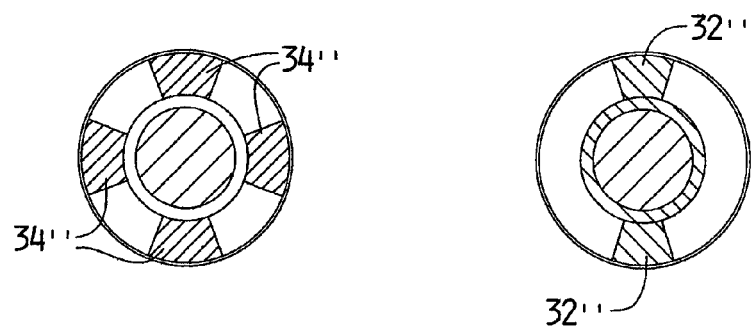

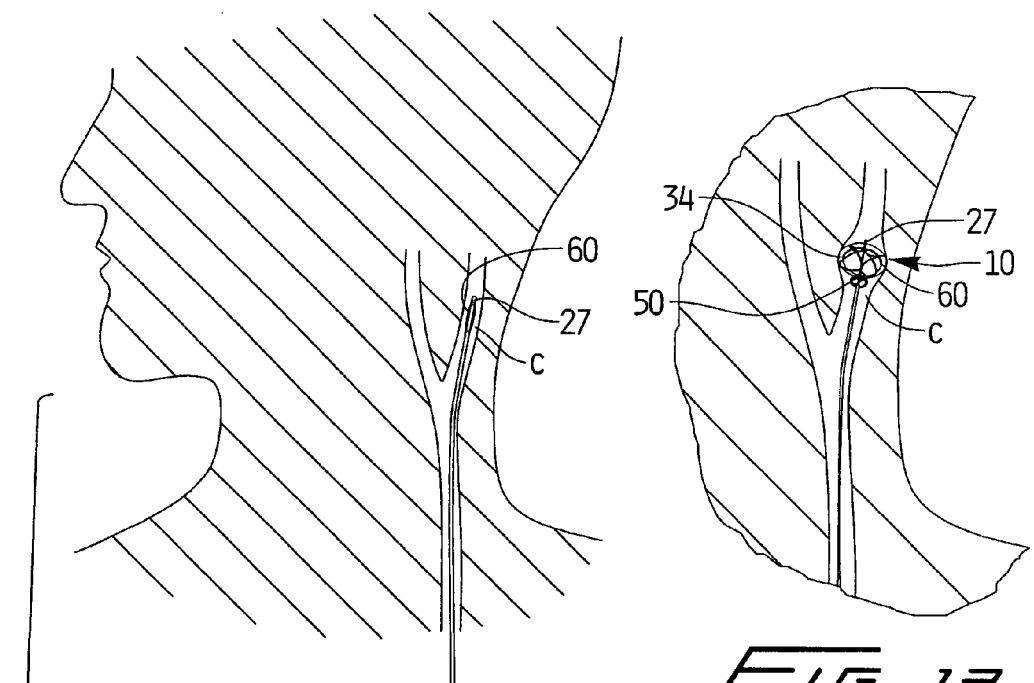
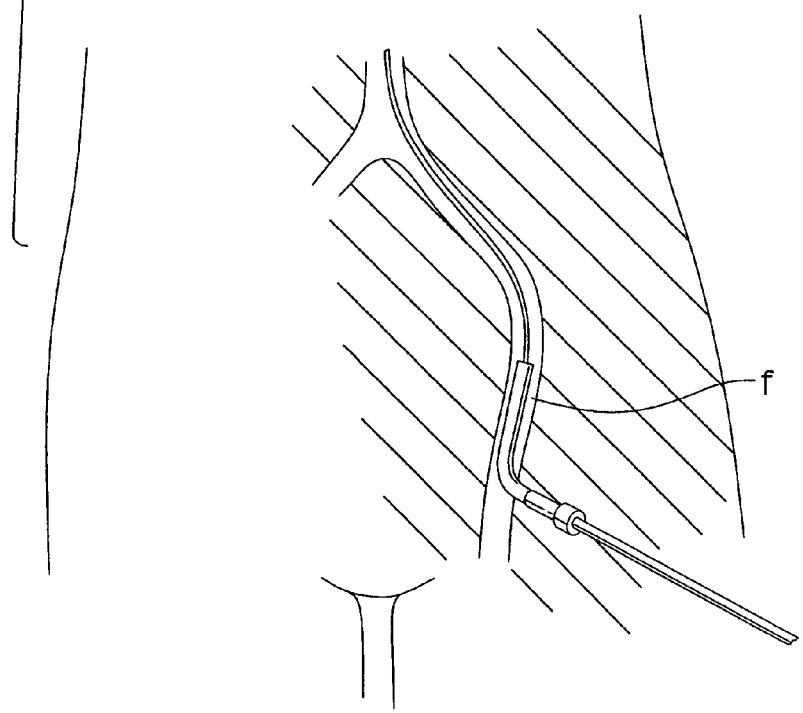

DISTAL PROTECTION DEVICE

This application claims priority from U.S. provisional application Ser. No. 60/466,491, filed Apr. 29, 2003, the entire contents of which are incorporated herein by reference.

BACKGROUND

1. Technical Field

This application relates to a vascular device and more particularly to a vascular device for capturing embolic material during surgical procedures.

2. Background of Related Art

During vascular surgical procedures such as stenting, angioplasty, thrombectomy, and atherectomy, embolic material such as plaque and blood clots can become dislodged. Dislodgement of such embolic material can cause the emboli to flow downstream to lodge in the vascular system, thereby occluding the flow of oxygenated blood to the brain or other vital organs. Such occlusion can compromise peripheral circulation resulting in amputation, or result in heart attack, stroke or even death.

Techniques to cut the debris into smaller sizes, such as by use of lasers, have had significant drawbacks, such as the inability to ensure all the debris is cut into sufficiently small fragments. If some of the fragments remain too large, then occlusion of the vessels can occur causing the problems and risks enumerated above.

Attempts have been made to place a device distal (downstream) of the stenosis, thrombus, etc. to capture the emboli. Such distal protection devices typically are collapsible for insertion and expandable once in the vessel. Some devices are in the form of an expandable balloon which is inserted within the vessel inside a sheath. When the sheath is withdrawn, the balloon is expanded to block emboli. These balloon devices even in the collapsed position increase the profile of the device since they are wrapped on the outside of the device. In other distal protection devices, a wire is covered by a membrane. These wires extend laterally from the device and may not enable the membrane to block the entire region of the vessel. Failure to expand to a geometry to block the entire region can result in the unwanted passage of debris which can cause vessel occlusion and the aforementioned adverse consequences.

The need therefore exists for an improved distal protection device. Such device would have a reduced profile to facilitate insertion and to better enable placement of the device distal of the emboli to block potential downstream flow. The device would also be easy to manipulate and sufficiently fill the vessel area to ensure all passage is blocked. The device would further be configured to avoid unwanted collapse during use.

It would also be desirable to provide a distal protection device which meets the above criteria plus has the advantage of accommodating various sized blood vessels. There is a tradeoff between providing large expansion of a distal protection device to block large blood vessels while ensuring that such large expansion would not damage a small blood vessel. Therefore, it would be advantageous to provide a single device which can expand sufficiently to effectively block embolic material without damaging the vessel, thus avoiding having to use different devices to accommodate different vessel sizes.

SUMMARY

The present invention overcomes the problems and deficiencies of the prior art. The present invention provides a distal protection device comprising a catheter having a first strut movable from a collapsed configuration to an expanded configuration and a second strut axially spaced from the first strut and movable from a collapsed configuration to an expanded configuration. The first strut has a first dimension and the second strut has a second dimension larger than the first dimension. The first and second struts are separately deployable. Movement of the first strut deploys filtering material to a first position having a first deployed dimension and movement of the second strut to a first position deploys filtering material to a second deployed dimension larger than the first deployed dimension.

In one embodiment, the same filtering material overlies both the first and second strut. In another embodiment, separate filtering materials overly the first strut and the second strut, but preferably the same type of material. In one embodiment, the material is a wire braid composed of a shape memory metal.

In one embodiment, the first strut is positioned proximal of the second strut. In another embodiment, the first strut is positioned distal of the second strut. Preferably, the struts are formed from a laser cut tube.

Preferably, the first and second struts are deployed laterally of the catheter and each form loops opening in a direction substantially aligned with blood flow such that the plane of the loop opening is substantially transverse to the direction of blood flow and substantially parallel to a transverse axis of the catheter.

The device may further comprise an actuating member slidably positioned within the catheter such that initial movement initially moves either the first strut or second strut from the collapsed position to the expanded configuration to form a loop. In a preferred embodiment, further movement of the actuating member moves the remaining collapsed strut to the expanded configuration to also form a loop.

The present invention also provides a distal protection device comprising a tube having a plurality of cutouts forming at least one distal elongated strut and at least one proximal elongated strut. The struts are movable from a retracted (collapsed) to an expanded position. Filter material overlies at least a portion of the struts and an actuating member is operatively connected to a portion of the tube wherein movement of the actuating member moves the portion of the tube to thereby move the distal elongated strut and the proximal elongated strut to the expanded position.

In a preferred embodiment, movement of the actuating member in a first direction retracts the portion of the tube to compress and thereby expand the elongated struts and movement of the actuating member in a reverse direction advances the portion of the tube to move the elongated strut to the retracted position.

In one embodiment the distal elongated strut(s) has a length greater than a length of the proximal elongated strut(s) such that upon expansion the distal elongated strut expands to a transverse dimension greater than a transverse dimension of the proximal strut. In another embodiment, the distal elongated strut(s) has a length smaller than a length of the proximal elongated strut(s) such that upon expansion the distal elongated strut expands to a transverse dimension smaller than a transverse dimension of the proximal strut.

In one embodiment, the filter material comprises a first material positioned over the distal elongated strut(s) and a separate material, preferably of the same composition (type), positioned over the proximal elongated strut(s). In another embodiment, the filter material overlies both the distal and proximal elongated struts. In one embodiment, the filter material comprises a wire braid composed of a shape memory material. In one embodiment, the filter material automatically moves back from an expanded position to a collapsed position upon movement of the at least one strut to the retracted position.

Preferably, the elongated struts form loops having a loop opening lying in a plane substantially transverse to a longitudinal axis of the tube and substantially parallel to a transverse axis of the tube.

The present invention also provides a distal protection device comprising a catheter having a tube formed with cutouts therein to form a first set of elongated struts and a second set of elongated struts. The elongated struts are movable between a retracted (collapsed) position and an expanded position wherein the distance between the proximal end and distal end of the struts in the retracted position is a first distance and the distance between the proximal end and distal end of the struts in the expanded position is a second distance less than the first distance. In the expanded position, the struts form loops with an opening lying in a plane substantially parallel to a transverse axis of the catheter and substantially transverse to the direction of blood flow. Filter material is deployable by the loops of the struts. The first set of struts is separately movable from the second set of struts to the expanded position to enable selective actuation of the set of struts to accommodate different sized vessels.

In one embodiment, the first set of elongated struts has a smaller buckling force than the second set of elongated struts such that upon actuation of an actuating member, the first set of elongated struts buckles fully to its expanded position and upon further actuation, the second set of elongated struts buckles fully to its expanded position.

In one embodiment, the tube forms first and second collars, and an actuating member is connected to the second collar such that the actuating member retracts the second collar to compress and thereby expand the elongated struts, and the first collar further acts as a stop.

BRIEF DESCRIPTION OF THE DRAWINGS

Preferred embodiment(s) of the present disclosure are described herein with reference to the drawings wherein:

FIG. 1 is a perspective view of a first embodiment of the distal protection device of the present invention in the collapsed position (the filtering material is removed for clarity);

FIG. 1A is an exploded view of the device of FIG. 1 (the filtering material is removed for clarity);

FIG. 1B is an enlarged view of a distal portion of the device of FIG. 1;

FIG. 2 is a transverse cross-sectional view taken along lines 2-2 of FIG. 1;

FIG. 3 is a transverse cross-sectional view taken along lines 3-3 of FIG. 1;

FIG. 3A is a longitudinal cross-sectional view of the device of FIG. 1 in the collapsed position;

FIG. 3B is a longitudinal cross-sectional view of the device of FIG. 1 showing the first set of struts and filtering material in an expanded position;

FIG. 4 is a perspective view of the distal portion of the distal protection device of FIG. 1 showing the first set of struts and first capturing (filtering) element (material) partially expanded;

FIG. 5 is a view similar to FIG. 4 showing the first set of struts and capturing element almost fully expanded;

FIG. 5A is a front view of the device of FIG. 5;

FIG. 6 is a view similar to FIG. 4 showing the first set of struts and first capturing element fully expanded and the second set of struts and second capturing (filtering) element (material) partially expanded;

FIG. 7 is a view similar to FIG. 4 showing the first and second sets of struts and first and second capturing elements fully expanded;

FIG. 8 is a view similar to FIG. 7, (both sets of struts expanded) except showing an alternate embodiment having a single capturing (filtering) element (material);

FIG. 9 is a perspective view of the distal portion of the distal protection device showing an alternate embodiment wherein the smaller capturing element is positioned distal of the larger capturing element;

FIG. 10 is a view similar to FIG. 9 showing an alternate embodiment having a single capturing element expandable by the first and second sets of struts;

FIG. 11A is a view similar to FIG. 7 showing an alternate embodiment of the capturing elements composed of a wire braid;

FIG. 11B is a perspective view of an alternate embodiment of the distal protection device having first and second sets of struts of different configuration, and shown in the collapsed configuration (the filtering material is removed for clarity);

FIGS. 11C and 11D are transverse cross-sectional views taken along lines 11C and 11D, respectively, of FIG. 11B; and FIGS. 12 and 13 illustrate placement of the device of FIG. 1, wherein FIG. 12 shows the catheter advanced through the femoral to the carotid artery and FIG. 13 shows the device deployed in the carotid artery to block distal flow of emboli.

DETAILED DESCRIPTION OF PREFERRED EMBODIMENTS

Referring now in detail to the drawings where like reference numerals identify similar or like components throughout the several views, several different embodiments for capturing embolic material during surgical procedures are disclosed. In each of the embodiments, two filtering devices are provided, with each filtering device designed to block embolic material while maintaining blood flow therethrough. The filtering devices are deployable to different transverse dimensions to accommodate different size vessels as described in more detail below.

Turning first to the embodiment illustrated in FIGS. 1-7, the distal protection device 10 includes a catheter having an outer tube 11, an internal coupler 14, a distal tube 16, a first capturing element 50 and a second capturing element 60. The capturing (filtering) elements 50 and 60 are movable between collapsed and expanded positions by struts 32, 34, respectively, formed in tube 16. As shown in FIGS. 3-7, first capturing element 50 is positioned proximally of second capturing element 60. As will be explained in further detail below, the capturing elements 50, 60 expand to different diameters to accommodate different sized vessels. The struts 32, 34 are formed so that relative movement of portions of the tube 16 expands the struts 32, 34. That is, an actuating member such as a shaft or wire 22 is slidably positioned within outer tube 11 and attached to a distal portion of tube 16. When actuating wire 22 is retracted, it moves a portion of the distal tube 16 proximally to expand the struts 32, 34, as explained in more detail below. Coupler 14 connects the tube 16 to the outer tube 11. The proximal end of coupler 14 is bonded, glued or attached by other means inside the outer tube 11. The distal tube 16 is slid over the coupler 14 and bonded or glued (or otherwise attached) thereto.

Turning to the distal tube 16, the struts 32, 34 are preferably formed by elongated slots or cutouts 37, 38, respectively, in the tube 16 (see e.g. FIGS. 1 and 1A). These slots 37, 38 are preferably formed by laser cutting the tube 16 although other ways to cut the slots are also contemplated. As formed, the slots 37, and therefore the struts 32, have a smaller length than the length of the slots 38 and struts 34. In one embodiment, in the collapsed position, the length L1 of the struts 32 is about 10 mm and the length L2 of the struts 34 is about 20 mm. Other dimensions are also contemplated.

The distal tube 16 is formed so that a first collar 40 is at the terminal end 33 of struts 32 and a second collar 42 is at the terminal end 43 of struts 34 (see FIGS. 1 and 1A). Thus, struts 32 extend from proximal tube end 17 to first collar 40 and the second longer struts 34 extend from first collar 40 to second collar 42 at the end of tube 16.

A radiopaque tip 27 is attached, e.g. by soldering, to the second or distal collar 42. This tip 27 guides the catheter and enables imaging of the catheter.

Inner actuating shaft or wire 22 is positioned within the outer tube 11 and is connected at its distal end to the collar 42 of distal tube 16. The proximal end 17 of the tube 16 can be fixed to tube 11 and/or coupler 14. Thus, sliding movement of the actuating wire 22 slides the collars 40, 42 proximally to compress the struts 32, 34. That is, upon proximal movement of the actuating wire 22 in the direction of the arrow of FIG. 4, the collars 40, 42 move proximally, thus forcing struts 32 and 34 outwardly as shown in FIGS. 4-7. Initially, upon retraction of wire 22, struts 32 will buckle first as shown in FIG. 5 since due to their reduced length the buckling force is less than the buckling force of the longer struts 34. The struts 32 will continue to buckle until the proximal surface 49 of collar 40 abuts the distal surface 15 of coupler 14. (See FIG. 5 which shows almost complete expansion of the struts 32, the remaining expansion corresponding to the remaining distance between proximal surface 49 and distal surface 15). Thus, coupler 14 (or collar 40) acts as a stop.

To further lower the buckling force, the shorter struts could be made thinner than the longer struts, such as shown for example in FIGS. 11B, 11C, and 11D, wherein struts 32″ have a diameter less than the diameter or thickness of the longer struts 34″ of device 10″.

The buckling forces can also be changed by modifying the resistance of movement of the respective collars.

Referring to FIG. 6, after struts 32 buckle, further proximal movement of actuating wire 22 continues to move collar 42 as movement of collar 40 is stopped by abutment with coupler 14. That is, since proximal movement of collar 40 at this point is stopped by abutment of collar 40 with the surface 15 of inner coupler 14, further proximal movement will further retract only collar 42, causing longer struts 34 to buckle outwardly to their fully expanded position shown in FIG. 7. Thus, the reduction of the distance between the collars 40, 42 forces the struts to compress and extend radially outwardly as shown in FIG. 7.

The expansion movement of the struts 32, 34 causes the overlying filter material 50, 60 to be deployed, moving to an expanded position. As shown, the filter material 50, 60 can be a polymeric membrane, such as polyurethane or PET, which is expanded by the struts 32, 34. A mouth or opening 52, 62 (see FIGS. 4 and 6) is provided at the proximal end of the filter material The polymeric material would have small holes dimensioned for allowing blood flow while blocking embolic material. Thus, embolic material exceeding a certain size carried by the blood is captured with smaller particles flowing through the holes or pores in the membrane. Alternatively, as shown in FIG. 11A, the filter of device 110 can be a tightly wound metal braided material such as shape memory metal, e.g. Nitinol. Thus, braided filtering material 150 overlies struts 132 and braided filtering material 160 overlies struts 134. The filtering material 150, 160 can also include a mouth or opening. Actuating member 122 moves the collars 140, 142 in the same manner as actuating member 22 of FIG. 1.

Preferably, the filtering material will be selected so that after it is radially stretched to an expanded configuration to block and capture flow of embolic material, it automatically retracts once the struts 32, 34 are moved to their collapsed position, as described in more detail below. In one embodiment, such as shown in the embodiments of FIGS. 1-7, a first filter material overlies struts 32 and a separate second filter material overlies struts 34. The separate material is preferably of the same type of material, however alternately it could be composed of a different material. In an alternate embodiment, shown in FIG. 8, rather than two separate filters, a single filtering material 64 is provided. One portion 65 of filter material 64 overlies struts 34 in its entirety while portion 63 overlies only a portion of struts 32, leaving an opening 67. Similarly, in the embodiment of the braided material, two separate elements can be provided as in FIG. 11A or alternatively a single filtering element could be provided overlying both sets of struts.

Referring back to the struts 32, 34, in the initial collapsed configuration, struts 32 and 34 are aligned with the outer surface of the distal tube 16 (and collars 40, 42) which is aligned with outer tube 11 to enable smooth insertion into the vessel and keep the overall insertion profile at a minimum. Proximal struts 32, when moved from a collapsed (retracted) position to an extended (expanded) position, each form a looped configuration, the loops designated by reference numeral 38. Thus, the struts 32 are forced out laterally to bend into a loop 38 (see FIG. 5). End 47A extends proximally and end 47B extends distally. The expanded loop 38 thus, has an opening 39 preferably lying in a plane substantially perpendicular to the longitudinal axis and substantially parallel to the transverse axis of the catheter. That is, the loop opening 39 lies in a plane substantially transverse to the direction of blood flow so the loop opening is substantially in line with the blood flow. In one embodiment, the loop opening plane can be at 90 degrees to the longitudinal axis. In another embodiment, it can be offset so it is at angle of less than 90 degrees, but preferably greater than about 45 degrees. In such embodiment, each strut 32 extends such that the loop opening 39 is slightly offset from the direction of the transverse axis of the catheter (and tube 16) but is still open generally in the direction of blood flow (for example, a 60 degree angle). Thus, in this embodiment, a central longitudinal axis extending through the loop opening could be at a small angle rather than parallel to the longitudinal axis of the tube 16, preferably less than 45 degrees to maintain the opening substantially in the direction of blood flow.

The formation of the loop stretches the membrane or filtering element to block the flow of material. In the membrane or braid, windows can be provided with enlarged openings for blood flow, with the membrane or braid blocking flow of materials exceeding the pore size. Alternatively, the material can have an open mouth region as illustrated and described above.

The shorter struts 32 preferably form two looped regions 39 when expanded so the filter material stretches in two directions. When slidable wire 22 is retracted in the direction of the arrow of FIG. 4 so the struts 32 buckle as described above, two looped regions are formed, one on one side of the catheter and the second looped wire region on the other side of the catheter, preferably about 180 degrees apart as depicted in FIG. 5. This double looped configuration causes the filter material to be expanded on opposing sides of the tube 16 and preferably blocking a 360 degree area. Although two struts 32 are shown, more struts 32 could be provided. Also, alternatively a single strut could be provided.

The second longer struts 34 form four looped regions 41 when expanded since four struts 34 are provided. When slidable wire 22, is retracted in the direction of the arrow and the struts 34 buckle as described above, four looped regions are formed, preferably about 90 degrees apart, causing filter material to be expanded radically on multiple sides of the tube 16 as illustrated in FIG. 7 and preferably blocking a 360 degree area. As in the loops of struts 32, the loops 38 open generally in a direction of blood flow, with the openings in the loop being substantially parallel to the transverse axis of the tube 16, and the loop opening plane being substantially perpendicular to the longitudinal axis and transverse to the direction of blood flow. As in loops 39, the plane of the opening of loop 38 in one embodiment is 90 degrees with respect to the longitudinal axis and parallel to the transverse axis. In another embodiment it is offset to form an angle of less than 90 degrees, but preferably greater than 45 degrees. Although four loops are shown, fewer or greater number of struts could be utilized.

In the alternate embodiments of FIGS. 9 and 10, the distal protection device 210 has shorter length struts distal of the larger struts. More specifically, referring first to FIG. 9, distal protection device 210 has two elongated struts 232 positioned distal of elongated struts 234. Actuating wire or shaft 222 is pulled proximally to retract collars 242, 240 to expand the respective struts 232, 234. Struts 232 buckle first, followed by buckling of longer struts 234.

Filtering material 250 overlying struts 232 is expanded to a smaller dimension than filtering material 260 overlying struts 234. In the alternate embodiment of FIG. 10, instead of the separate filtering materials, a single filtering material 270 overlies struts 232' and 234' of distal protection device 210'. Otherwise the embodiment of FIGS. 9 and 10 are the same and corresponding parts are designated "prime". Alternatively, both sets of struts can begin to buckle simultaneously, or the longer struts can begin to buckle first, followed by additional expansion of the shorter struts first. The longer struts, however, would not fully expand until the shorter struts fully expand.

In the preferred embodiment, the catheter has a length of about 135 cm to about 300 cm. The diameter of the catheter is preferably about 0.010 inches to about 0.030 inches and more preferably about 0.018 inches to enable low profile insertion into the vessel. The first capturing element 50, when expanded, preferably has a diameter from about 1 mm to about 4 mm. The second capturing element 60, when expanded, preferably has a diameter from about 4 mm to about 9 mm.

In use, if the vessel is a smaller size, e.g., 2 mm, only the smaller capturing element 50 would be deployed. If the vessel is a larger size, after deployment of the first capturing element 50, the second capturing element 60 would be deployed in the manner described above.

To withdraw the device 10, the actuating wire 22 is pushed distally to advance collars 40, 42 to retract the loops as the struts 32, 34 return to their collapsed positions to enable the filter material to return to the initial low profile collapsed insertion position. In a preferred embodiment, the filter is made of a material that would return automatically from its stretched position to the original collapsed position when the wire 22 is pushed distally. One way this could be achieved is by use of the shape memory material with a memorized position in the collapsed position. This passive self-contraction would avoid the need for insertion of a separate device or sheath over the filter material to cover it for removal, thus reducing the overall profile of the instrumentation necessary for the procedure. That is, in the preferred embodiment, the wire 22 and thus the struts 32, 34 are expanded by active control while the filter material would automatically retract without other assistance.

In another embodiment, the filter material can be attached to the struts 32, 34 and thereby move with the actuating wire 22 between the collapsed and expanded positions.

Being part of a guidewire, in use, the distal protection devices described herein, can be used for initial introduction of a catheter. The distal protection device could also be placed within a catheter after the guidewire for introducing the catheter is withdrawn. The catheter can then be withdrawn and another catheter, such as a stent delivery catheter, could be inserted over the distal protection device. As other catheters can be inserted over the device, it further functions as a guidewire.

FIGS. 12-13 show the positioning of the distal protection device 10 of the present invention in a larger vessel when deployment of the larger struts is desirable. These Figures show the device 10 inserted by way of example, as the other devices described herein can be inserted and placed in a similar manner. Device 10 of FIG. 1 is shown deployed in the carotid artery "c". The introducer is inserted through the femoral vein "f" as shown in FIG. 12. The device 10 is advanced through the femoral vein to the carotid artery "c". Once positioned at the desired site, the actuating wire is retracted as described above to deploy both sets of struts 32, 34 to the looped configuration to expand the filter material 50 and larger filter material 60 to block emboli in the artery.

It should be appreciated that the terms "first and second" as used herein are used for the readers' convenience. Also, proximal refers to the region closer to the user and distal to the region further from the user, again used for the readers' convenience.

While the above description contains many specifics, those specifics should not be construed as limitations on the scope of the disclosure, but merely as exemplifications of preferred embodiments thereof. For example, different filter materials can be utilized such as polymeric material, a composite of a polymeric material and metallic material or metal fibers, an elastomeric material, or a composite of elastomeric and metallic material. (Examples of polymeric material include polyester, PET, LDPE (low density polyethylene), HDPE; examples of elastomeric material include silicon and urethane; examples of metallic materials include stainless steel and shape memory Nitinol). Those skilled in the art will envision many other possible variations that are within the scope and spirit of the disclosure as defined by the claims appended hereto.

What is claimed is:

1. A distal protection device comprising a catheter having a tube formed with cutouts therein to form a first set of elongated struts and a second set of elongated struts, the tube having a longitudinal axis and a transverse axis transverse to the longitudinal axis of the tube each of the elongated struts having a proximal end and a distal end, the elongated struts being movable between a retracted position and an expanded position wherein the distance between the proximal end and distal end in the retracted position is a first distance and the distance between the proximal end and distal end in the expanded position is a second distance less than the first distance, in the expanded position the elongated struts forming loops with an opening lying in a plane substantially parallel to the transverse axis of the tube, and filter material deployable by the loops of the struts, the first set of struts and the second set of struts being separately movable to the expanded position to enable actuation of the first set of struts to accommodate a first size vessel and actuation of the second set of struts to accommodate a second different size vessel.

2. The device of claim 1, wherein the first set of elongated struts has a smaller buckling force than the second set of elongated struts such that upon actuation of an actuating member, the first set of elongated struts buckles fully to its expanded position and upon further actuation the second set of elongated struts buckles fully to its expanded position.

3. The device of claim 1, wherein the tube forms first and second collars and an actuating member is connected to the second collar such that the actuating member retracts the second collar to compress and thereby expand the elongated struts, and the first collar further acts as a stop.

* * * * *